United States Patent [19]
Suzuki et al.

[11] Patent Number: 5,145,781
[45] Date of Patent: Sep. 8, 1992

[54] PREPARATION AND USES OF ALPHA-GLYCOSYL RUTIN

[75] Inventors: Yukio Suzuki; Kei Suzuki; Masaru Yoneyama; Hiromi Hijiya; Toshio Miyake, all of Okayama, Japan

[73] Assignee: Kabushiki Kaisha Hayashibara Seibutsu Kagaku Kenkyujo, Okayama, Japan

[21] Appl. No.: 489,566

[22] Filed: Mar. 7, 1990

[30] Foreign Application Priority Data

| Mar. 8, 1989 | [JP] | Japan | 1-57299 |
| Apr. 15, 1989 | [JP] | Japan | 1-95999 |
| Jun. 6, 1989 | [JP] | Japan | 1-142205 |
| Aug. 24, 1989 | [JP] | Japan | 1-217893 |

[51] Int. Cl.$^5$ .............. C12P 19/14; C12P 19/20; C12P 19/18; C12P 19/44
[52] U.S. Cl. .............. 435/99; 435/74; 435/96; 435/97; 536/8; 536/124; 426/541; 426/658; 514/26; 514/844; 514/777; 252/397; 252/363.5
[58] Field of Search .............. 435/99, 96, 97, 74; 536/8, 124

[56] References Cited

U.S. PATENT DOCUMENTS

| 4,338,398 | 7/1982 | Yoneyama | 435/99 |
| 4,636,394 | 1/1987 | Hsu | 426/423 |
| 4,755,504 | 7/1988 | Liu | 536/6.3 |
| 4,774,229 | 9/1988 | Jordan | 536/121 |
| 4,837,006 | 6/1989 | Rosenbaum et al. | 424/72 |

FOREIGN PATENT DOCUMENTS

| 25-1677 | 6/1950 | Japan . |
| 26-2724 | 5/1951 | Japan . |
| 29-1285 | 3/1954 | Japan . |
| 54-32073 | 10/1979 | Japan . |
| 56-156299 | 12/1981 | Japan . |

OTHER PUBLICATIONS

Yamasaki et al., *Biological Abstracts*, vol. 66 (11), Dec. 1, 1978, #67094.
Majoie, *Chemical Abstracts*, vol. 95, Jul. 20, 1981, #25550d.
"Water Soluble Derivatives of Vitamin P," Japanese Patents Report, sec. CH, vol. 79, No. 42, Nov. 16, 1979, p. J7-B (Japanese Patent J79-032073).
"Preparation of Glycosyl Vitamins," Chemical Abstracts, vol. 96, No. 24, Jun. 14, 1982, p. 379, Abstract No. 205 400j (Japanese Patent J81-156,299).
"Flavonoids as Drugs", Chemical Abstracts, vol. 97, No. 7, Aug. 16, 1982, p. 518, Abstract No. 54 317e.

*Primary Examiner*—Ronald W. Griffin
*Assistant Examiner*—Pamela S. Webber
*Attorney, Agent, or Firm*—Browdy and Neimark

[57] ABSTRACT

Alpha-glycosyl rutin is formed at a high concentration by allowing a saccharide-transferring enzyme to act on a high-rutin content liquid in suspension or solution to effect saccharide-transfer reaction. The resultant alpha-glycosyl rutin is easily recovered from the reaction mixture by allowing it to contact with a synthetic macroreticular resin. Alpha-glycosyl rutin is superior in water-solubility, resistance to light and stability to intact rutin, as well as having the physiological activities as intact rutin has. Thus, alpha-glycosyl rutin is favorably usable as a yellow coloring agent, antioxidant, stabilizer, fading-preventing agent, quality-improving agent, preventive, remedy, uv-absorbent and deterioration-preventing agent in foods, beverages, tobaccos, cigarettes, feeds, pet foods, pharmaceuticals for susceptive diseases, cosmetics including skin-refining agent and skin-whitening agent, and plastics, in addition to the use in vitamin P-enriching agents.

23 Claims, No Drawings

PREPARATION AND USES OF ALPHA-GLYCOSYL RUTIN

BACKGROUND OF THE INVENTION

1. Field of the invention

The present invention relates to the preparation and uses of alpha-glycosyl rutin.

2. Description of the prior art Rutin, whose chemical structure is given below, has been known as a yellow pigment and vitamin P with physiological activities such as stabilization of blood vessels, prevention of hemorrhage and regulation of blood pressure, and used from ancient times in foodstuffs, pharmaceuticals and cosmetics.

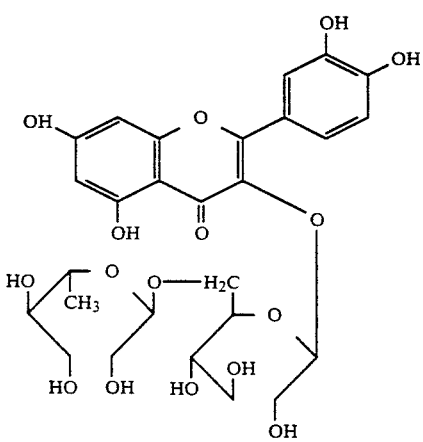

It is known that vitamin P takes part in some of the physiological activities of vitamin C in vivo; for example, in the hydroxylation of proline and lysine which are necessary to synthesize collagen as the main element of living connective tissues; the oxidation-reduction reaction of cytochrome C wherein $Fe+++$ is reduced into $Fe++$; and in the immunopotentiation via the increase of leukocyte. These are because vitamin P plays a significant role in the maintenance and promotion of health in living bodies.

Nowadays the use of rutin is not limited to agents which enrich vitamin P as a nutritive element, but is extending in various applications. More particularly, because of its chemical structure and physiological activities, rutin is useful as a yellow coloring agent and antioxidant alone or in combination with one or more vitamins, for example, in foods, beverages and pharmaceuticals for susceptive diseases such as preventive and remedy for circulatory diseases, as well as a yellow coloring agent and uv-absorbent in cosmetics such as skin-refining and skin-whitening agents.

Rutin is, however, hardly soluble in water (only about 1g in 8 liters of water or about 0.01 w/v % at ambient temperature). This renders its practical use very difficult.

To improve this low water-solubility, some methods have been attempted. For example, Japanese Patent Publication No.1,677/50 disclose a method wherein aliphatic compounds with amino groups are added to rutin for its increased water-solubility; Japanese Patent Publication No.2,724/51, another method wherein monohalogeno acetic acids are allowed to act on rutin to convert it into sodium monohalogeno acetates having an increased water-solubility; and Japanese Patent Publication No.1,285/54, one another method wherein "Rongalit", a commercialized sodium hydroxymethane, is allowed to act on rutin to convert it into sulfite compounds having an increased water-solubility.

These methods have, however, the drawback that the use of amino compounds, monohalogeno acetic acids and sulfite compounds may result in an undesirable physiological activity and/or toxicity in final products, as well as rendering their purification very difficult.

We proposed a much safer solubilization method in Japanese Patent Publication No.32,073/79, wherein a biosynthesis by saccharide-transferring enzyme is utilized to transfer equimolar or more glucose residues from a partial starch hydrolysate to rutin to form alpha-glycosyl rutin having an improved water-solubility.

The alpha-glycosyl rutin obtained by the method would have an extensive use because it exhibits the same physiological activities as does intact rutin, and is free from toxicity, highly soluble in water, and therefore easily handleable. Thus, the realization of alpha-glycosyl rutin has been in strong expectation.

Since alpha-glycosyl rutin has many advantages as described above, its commercialization has been in great demand.

However, the initial concentration for rutin, attainable by conventional methods, is about 0.1 w/v % at most, and this extremely increases and wastes water and energy cost for the preparation and purification of alpha-glycosyl rutin. This is one of the major causes which have hindered the commercialization of alpha-glycosyl rutin.

SUMMARY OF THE INVENTION

The present invention is to overcome the drawback of conventional method. We studied particularly reaction processes which provide an increased initial concentration for rutin, and purification processes for the resultant alpha-glycosyl rutin.

As the result, we found that alpha-glycosyl rutin is obtainable in a high yield by allowing a saccharide-transferring enzyme to act on a high-rutin content liquid which contains a high-concentration rutin together with an amylaceous substance, more particularly, by first preparing rutin into a high-concentration suspension or dissolving of rutin at an alkaline pH or in an aqueous organic solvent into a high-concentration solution, in either case, to give an initial concentration for rutin of about 0.5 w/v % or higher, desirably, about 1.0–20.0 w/v % which is about 5-folds or more, desirably, about 10–200-folds of that attainable by conventional methods, then allowing a saccharide-transferring enzyme to act on the highrutin content suspension or solution.

We also found that an alpha-glycosyl rutin mainly composed of alpha-glucosyl rutin and/or alpha-maltosyl rutin is obtainable in a high yield by first allowing a saccharide-transferring enzyme to act on a solution which contains rutin together with an amylaceous substance, then allowing amylase to act on the resultant mixture.

We accomplished the present invention by further establishing the use of the alpha-glycosyl rutin obtained by these method, for example, in foods, beverages, pharmaceuticals for susceptive diseases, cosmetics and antioxidants.

We reached still another finding that a reaction mixture containing alpha-glycosyl rutin can be easily purified by allowing it to contact with a synthetic macroreticular resin, and fractioning the mixture by utilizing the difference in adsorbability. When the reaction mixture contains an organic solvent, the alpha-glycosyl rutin can be purified similarly as above by decreasing the concentration of the organic solvent, and allowing the reaction mixture to contact with a synthetic macroreticular resin.

Thus, we confirmed that the process according to the present invention extremely reduces and saves the water and energy required for the reaction and purification of alpha-glycosyl rutin, thus completely overcoming the drawback of conventional method and extremely facilitating the commercialization of alpha-glycosyl rutin.

DETAILED DESCRIPTION OF THE INVENTION

The rutin usable in the invention shall not be limited to those in highly-purified form. For example, mixtures with flavonoid glycosides such as citronin, naringin and hesperidin, and intact and partially-purified extracts from plant tissues are suitable, as long as they contain rutin.

Examples of such plant tissues are leaves and stems of buckwheat plant (Fagopyrum esculentum), eucalyptus and ginkgo tree (Ginkgo biloba); "kaika" or "kaibei", flower buds of Japanese pagoda tree (Sophora japonica); flower buds of common broom (Cytisus scoparius); and citrus fruits.

The amylaceous substances usable in the invention are those which permit a saccharide-transferring enzyme to act on rutin to form alpha-glycosyl rutin wherein equimolar or more glucose residues are bound to rutin. For example, partial starch hydrolysates such as amylose, dextrin, cyclodextrin and maltooligosaccharide, liquefied starch, and gelatinized starch are suitably chosen.

Consequently to facilitate the formation of alpha-glycosyl rutin, it is recommendable to choose for the particular saccharide-transferring enzyme an amylaceous substance having an adequate susceptivity thereto.

For example, in the case of using alpha-glucosidase (EC 3.2.1.20) as the saccharide-transferring enzyme, maltooligosaccharides such as maltose, maltotriose and maltotetraose are suitable, as well as partial starch hydrolysates having a DE (dextrose equivalent) in the range of about 10-70. When cyclomaltodextrin glucanotransferase (EC 2.4.1.19) is used as the saccharide-transferring enzyme, gelatinized starches having a DE of below 1 and partial starch hydrolysates having a DE up to about 60 are suitable, as well as cyclodextrins. When alpha-amylase (EC 3.2.1.1) is used as the saccharide-transferring enzyme, gelatinized starches having a DE of below 1 and dextrins and partial starch hydrolysates having a DE up to about 30 are suitable.

The concentration of such an amylaceous substance during the reaction is set to a level which is about 0.5-50-fold higher than that of rutin.

The wording "high-rutin content liquid" as referred to in the invention means those which contain a high-concentration of rutin. For example, a solution containing rutin at a high concentration which is obtainable by dissolving rutin at a pH exceeding 7.0 or dissolving rutin in an aqueous organic solvent is suitable, as well as a suspension which contains rutin at a high concentration. More particularly, the wording means suspension and solution which have a rutin content of about 0.5 w/v % or higher, desirably, about 1.0-20.0 w/v %.

The organic solvents usable in the present invention are those which increase the solubility of rutin as compared to that in water. For example, water-miscible lower alcohols and ketones such as methanol, ethanol, n-propanol, isopropanol, n-butanol, "ACETOL ®" (1-hydroxyl-2-propanone)" and acetone are suitable.

The concentration of such an organic solvent is set to a level which gives the possible highest concentration for rutin and promotes the formation of alpha-glycosyl rutin, but insolubilizes both amylaceous substance and saccharide-transferring enzyme as little as possible; usually, about 3-70 v/v %, desirably, about 5-60 v/v %.

To facilitate dissolution to the possible highest concentration, a solution which is obtainable by dissolving rutin in an aqueous alkaline solution, such as those of sodium hydroxide and ammonia, is mixed with an aqueous organic solvent and neutralized, prior to the saccharide-transfer reaction.

The saccharide-transferring enzymes usable in the present invention are those which form alpha-glycosyl rutin without decomposing rutin when allowed to act on a high-rutin content liquid which additionally contains an amylaceous substance having an adequate susceptivity to the enzyme.

Examples of such a saccharide-transferring enzyme are alpha-glucosidases derived from animal and plant tissues such as pig lever and buckwheat seed, and from a culture obtainable by cultivating in a nutrient culture medium microorganisms including bacteria, molds and yeasts, for example, those of the genera Mucor, Penicillium and Saccharomyces; cyclomaltodextrin glucanotransferases derived from a culture of bacteria such as those of the genera Bacillus and Klebsiella; and alpha-amylases derived from a culture of fungi such as those of the genus Aspergillus.

Such a saccharide-transferring enzyme should not necessarily be purified prior to its use, as long as it fulfills the above requirements. Generally, the present invention is feasible with a crude enzyme.

If necessary, saccharide-transferring enzymes can be purified by conventional methods, prior to their use. Of course, commercialized saccharide-transferring enzymes can be used in the invention.

In the course of the reaction, the pH and temperature are set to a level where a saccharide-transferring enzyme forms alpha-glycosyl rutin; usually, at a pH in the range of 3-10 and a temperature in the range of 10-90° C.

The amount of saccharide-transferring enzyme and reaction time are closely dependent an each other. With an economical viewpoint, saccharide-transferring enzyme is used in an amount which completes the reaction within about 5-80 hours.

Immobilized saccharide-transferring enzymes can be suitably used batchwise and in continuous manner.

If necessary, alpha-glycosyl rutin can be produced by culturing a microorganism capable of producing a saccharide-transferring enzyme in a nutrient culture medium which contains rutin together with an amylaceous substance, or incubating in such a nutrient culture medium an animal- or plant-tissue which contains a saccharide-transferring enzyme.

The present invention is feasible with any reaction process, as long as it contains the step of allowing a saccharide-transferring enzyme to act on a high-rutin content liquid.

For example, in case that rutin is allowed to react at a high concentration in suspension, a high-rutin content liquid which contains about 0.5 w/v % or more, desirably, about 1.0–5.0 w/v % of rutin together with an appropriate amount of an amylaceous substance is subjected to a saccharide-transferring enzyme while keeping the pH to about 4.5–6.5 and the temperature to the possible highest level where the enzyme is active, in particular, in the range of about 70°–90° C. Thus, as the conversion into alpha-glycosyl rutin proceeds, the rutin in suspension gradually dissolves to promptly and readily form alpha-glycosyl rutin species such as alpha-glucosyl rutin, alpha-maltosyl rutin, alpha-maltotriosyl rutin, alpha-maltotetraosyl rutin, alpha-maltopentaosyl rutin and alpha-maltohexaosyl rutin at a high concentration. We confirmed that at ambient temperature the solution obtained in this way usually contains a large amount of alpha-glycosyl rutin and a small amount of the remaining rutin, and the total amount reaches about 0.5 w/v % or more, desirably, up to about 1.0–5.0 w/v % when calculated as rutin.

For example, in case that rutin is allowed to react at a high concentration in solution, a high-rutin content liquid which is obtainable by first dissolving about 0.5 w/v % more, desirably, about 1.0–5.0 w/v % rutin in water at a pH exceeding 7.0, in particular, pH 7.5–10, by heating, then dissolving in the resultant solution an appropriate amount of an amylaceous substance is subjected to a saccharide-transferring enzyme while keeping both pH and temperature to the possible highest levels where the enzyme is active, in particular, at a pH in the range of about 7.5–10.0 and a temperature in the range of about 50°–80° C. Thus, alpha-glycosyl rutin is readily formed at a high concentration. In this case, since rutin tends to readily decompose in an alkaline solution, desirably, the liquid is kept under light-shielding and unaerobic conditions in order to prevent the decomposition.

We confirmed that at ambient temperature the solution obtained in this way usually contains a large amount of alpha-glycosyl rutin and a small amount of the remaining rutin, and the total amount reaches about 0.5 w/v % or more, desirably, about 1.0–10 w/v % when calculated as rutin.

For example, in case that rutin is allowed to react in a high-concentration solution in an aqueous organic solvent, a solution which is obtainable by dissolving rutin in an organic solvent by heating is mixed with an amylaceous substance in aqueous solution, and then added with a saccharide-transferring enzyme. Alternatively, rutin and an amylaceous substance are dissolved in an aqueous organic solvent by heating, and the resultant solution is cooled to a prescribed temperature and added with a saccharide-transferring enzyme.

We confirmed that the solution obtained in this way usually contains a large amount of alpha-glycosyl rutin and a small amount of the remaining rutin, and the total amount reaches up to about 1.0–10 w/v % when calculated as rutin.

Alpha-glycosyl rutin can be formed at a high concentration similarly as above by the combination of two or more procedures; for example, by first keeping at a pH in the range of about 7.5–10.0 and a temperature in the range of 50°–80° C. a high-rutin content liquid which contains in suspension an about 2.0–20.0 w/v % rutin together with an appropriate amount of an amylaceous substance, then subjecting the liquid to a saccharide-transferring enzyme.

Also alpha-glycosyl rutin can be readily formed at a high concentration by dissolving rutin in a strongly alkaline aqueous solution, for example, about 0.1–1.0N aqueous solutions of sodium hydroxide, potassium hydroxide, sodium carbonate, calcium hydroxide and ammonia, to give a concentration of about 5.0–20.0 w/v %; adjusting the resultant solution with an aqueous solution of an acid such as hydrochloric acid and sulfuric acid to a pH level where a saccharide-transferring enzyme is active; adding an amylaceous substance to the solution; and promptly subjecting the solution to the enzyme. In this case, since the pH adjustment in an aqueous acidic solution tends to cause sedimentation in a high-rutin content solution, desirably, the saccharide-transfer reaction is initiated while suppressing the sedimentation by adding an amylaceous substance and/or a small amount of alpha-glycosyl rutin, prior to the pH adjustment. We confirmed that at ambient temperature and approximately neutral pH the solution obtained in this way usually contains a large amount of alpha-glycosyl rutin and a small amount of the remaining rutin, and the total amount reaches up to about 5.0–20.0 w/v % when calculated as rutin.

If necessary, in order to increase the solubility of rutin to facilitate the saccharide-transfer reaction thereto, one or more water-miscible organic solvents, for example, lower alcohols and ketones such as methanol, ethanol, n-propanol, isopropanol, n-butanol, ACETOL and acetone, can be favorably added to a high-rutin content liquid, prior to the reaction.

As mentioned above, we confirmed that the process according to the invention increases the initial concentration for rutin to a level which is about 5-fold or much higher, desirably, about 10–200-fold higher than that attainable by conventional method, and this facilitates the formation of alpha-glycosyl rutin at a high concentration.

More particularly, on the completion of the reaction, the reaction mixture contains in solution a large amount of alpha-glycosyl rutin and a small amount of the remaining rutin, and the total amount is about 0.5 w/v % or more, desirably, up to about 1.0–20.0 w/v % when calculated as rutin, which is about 5-fold or much higher, preferably, about 10–200-fold or much higher than that attainable by conventional method.

The alpha-glycosyl rutin having a relatively high molecular weight, formed by the saccharide-transfer reaction, is partially hydrolyzable with an amylase such as glucoamylase (EC 3.2.1.3) and beta-amylase (EC 3.2.1.2) intact or after purification with a synthetic macroreticular resins. Such hydrolysis adequately reduces the polymerization degree of alpha-D-glucosyl moieties in the alpha-glycosyl rutin. For example, glucoamylase hydrolyzes alpha-maltosyl rutin and higher products to accumulate glucose and alpha-glucosyl rutin, while beta-amylase hydrolyzes alpha-maltotriosyl rutin and higher products to accumulate maltose and a mixture which is mainly composed of alpha-glucosyl and alpha-maltosyl rutins.

The reaction mixture thus obtained may be prepared into final products without no further special treatment. Usually, the reaction mixture is filtered and concentrated into a syrupy product which is, if necessary, dried and prepared into a powdery product.

In addition to the use in vitamin P-enriching agent, the products are favorably usable as a highly-safe, natural yellow coloring agent, antioxidant, stabilizer, fading-preventing agent, quality-improving agent, preventive, remedy, uv-absorbent, deterioration-preventing agent in foods, beverages, tobaccos, cigarets, feeds, pet foods, pharmaceuticals for susceptive diseases, cosmetics and plastics.

In case that a purified alpha-glycosyl rutin product is needed, alpha-glycosyl rutin and contaminants including amylaceous substances are separated by utilizing the difference in adsorbability to a synthetic macroreticular resin.

The wording "synthetic macroreticular resin" as referred to in the invention means non-ionic, porous, synthetic resins which provide a large adsorptive area, such as styrenedivinylbenzen copolymer, phenol-formaldehyde resin, acrylic resin and methacrylate resins. Examples such as such a resin are "Amberlite XAD-1", "Amberlite XAD-2", "Amberlite XAD-4", "Amberlite XAD-7", "Amberlite XAD-8", "Amberlite XAD-11" and "Amberlite XAD-12", products of Rohm & Haas Company, Philadelphia, USA; "Diaion HP-10", "Diaion HP-20", "Diaion HP-30", "Diaion HP-40" and "Diaion HP-50", products of Mitsubishi Chemical Industries Ltd., Tokyo, Japan; and "Imac Syn-42", "Imac Syn-44" and "Imac Syn-46", products of Industrie de Maatshappily activate N.V., Amsterdam, Netherlands.

The purification process according to the invention contains the step of applying a reaction mixture containing alpha-glycosyl rutin, for example, to a column of a synthetic macroreticular resin so that the column adsorbs the alpha-glycosyl rutin and a relatively small amount of the remaining rutin, while large amounts of an amylaceous substance and water-soluble saccharides flows out through the column without causing adsorption.

Particularly in case that a reaction mixture contains an organic solvent, alpha-glycosyl rutin can be purified similarly as above by first decreasing the concentration of the organic solvent, then allowing the reaction mixture to contact with a synthetic macroreticular resin such that it adsorbs the alpha-glycosyl rutin and remaining rutin.

If necessary, after completion of the saccharidetransfer reaction but before treatment with a synthetic macroreticular resin, the reaction mixture can be treated by one or more methods; for example, a method wherein the reaction mixture is heated and the insolubilized substances are removed by filtration; another method wherein the reaction mixture is treated, for example, with either magnesium alumino silicate hydrate or magnesium aluminate to adsorb the proteinaceous substances for their removal; and one another method wherein the reaction mixture is deionized with a strongly-acidic ion exchange (H-form) and/or a neutral or slightly-alkaline ion exchange (OH-form).

A column of a synthetic macroreticular resin on which alpha-glucosyl rutin and a relatively small amount of the remaining rutin are specifically adsorbed are washed with a diluted alkali or water, and then applied with a relatively small amount of an organic solvent or mixture with water, for example, aqueous methanol and aqueous ethanol. Thus, the alpha-glycosyl rutin first elutes, while the intact rutin can be eluted by continuing the application or increasing the concentration of the organic solvent.

The obtained eluate rich in alpha-glycosyl rutin is distilled to remove the organic solvent, and concentrated to an adequate level. Thus, one can obtain a syrupy product mainly composed of alpha-glycosyl rutin. Subsequent drying and pulverization of the product yield a powdery product mainly composed of alpha-glycosyl rutin.

The elution operation using organic solvents simultaneously regenerates synthetic macroreticular resins, and this enables its repeated use.

The purification process using synthetic macroreticular resins is characterized in that it can remove, in addition to amylaceous substances and water-soluble saccharides, other concomitants including water-soluble salts. The alpha-glycosyl rutin thus obtained is characterized by:

(1) It is superior in water-solubility to intact rutin.
(2) It is higher in resistance to light and stability than intact rutin.
(3) It has a strong antioxidant activity. Because of this, it is favorably usable as an antioxidant in fatty foodstuffs, and pharmaceuticals for susceptive diseases and cosmetics containing oils and fats to prevent their oxidation. Particularly when used in pharmaceuticals, alpha-glycosyl rutin acts as an antioxidant to exhibit activities of removing activated oxygen and suppressing the formation of lipoperoxides, and this is convenient in the prevention and treatment of susceptive diseases and also in the maintenance and promotion of health. Unlike conventional antioxidants such as vitamin E and vitamin C, alpha-glycosyl rutin is substantially odorless and tasteless, and usable without fear of causing undesired coloration, browning and unpleasant odor.
(4) It is hydrolyzable into rutin and glucose by the in vivo enzyme system to exert the physiological activity inherent to rutin, in particular, vitamin P activity. Combination with vitamin C augments the physiological activities of both vitamins.
(5) When an alpha-glycosyl rutin product additionally contains an amylaceous substance, the alpha-glycosyl rutin component exhibits its inherent activities, while the amylaceous substance exhibits shape-imparting, filling and sweetening activities. A product free from amylaceous substance is substantially tasteless and odorless, and exhibits the activity of alpha-glycosyl rutin without causing substantial shape-imparting and increase in quantity. Thus, the product is freely usable in seasoning and flavoring.

Because of these, alpha-glycosyl rutin can be favorably incorporated as a yellow coloring agent, antioxidant, stabilizer, fading-preventing agent, quality-improving agent, uv-absorbent, preventive and remedy for susceptive diseases such as viral diseases, bacterial diseases, circulatory diseases and malignant tumors alone or in combination with one or more ingredients, desirably, in an amount of 0.001 w/w % or more in foods, beverages, tobaccos, cigarets, feeds, pet foods, pharmaceuticals for susceptive diseases, cosmetics such as skin-refining agents and skin-whitening agents, and plastics, as well as in agents which are directed to enrich a highly safe, natural vitamin P.

Since alpha-glycosyl rutin is highly resistant to acid and heat, and well harmonizes with various substances which taste sour, salty, bitter, delicious and astringent, it can be favorably incorporated as a vitamin P-enriching agent, yellow coloring agent, antioxidant, quality-improving agent and stabilizer in foods and beverages in general, for example, seasonings such as soy sauce, say sauce powder, miso, miso powder, "moromi", "hishio", "furikake", mayonnaise, dressing, vinegar, "sanbai-zu", "funmatsu-sushi-su", "chuka-no-moto", "tentsuyu (soup for tenpura)", "mentsuyu (soup for Japanese-style noodles)", Worcester sauce, ketchup, "yakiniku-no-tare (soup for grilled meat)", curry roux, stew premix, soup premix, "dashi-no-moto", mixed seasoning, "mirin (heavily sweetened sake)", "shin-mirin (synthetic mirin)", table sugar and coffee sugar; Japanese-style confectioneries such as "senbei (rice crackers)", "arare (pellet-shaped senbei)", "okoshi (millet-and rice cracker)", "karinto (fried dough cookie)", "gyuhi (starch paste)", rice paste, "manju (bun with a bean-jam filling)", "uiro (sweet rice jelly)", "an (bean jam)", "yokan (sweet jelly of beans)", "mizu-yokan (soft adzuki-bean jelly)", "kingyoku", jelly, castella and "amedama (Japanese-style toffee)"; Western-style confectioneries such as bun, biscuit, cracker, cookie, pie, pudding, cream puff, waffle, sponge cake, doughnut, chocolate, chewing gum, caramel and candy; ice cream and sherbet; syrups such as those for fruit preserve and "kaki-gori (shaved ice)"; spreads and pastes such as butter cream, custard cream, flour paste and fruit paste; processed fruits such as jam, marmalade, fruit syrup and preserved fruit; processed foods such as those of fruits and vegetables; cereals such as bakery product, noodle, vermicelli, boiled rice and synthetic meat; fatty food substances such as salad oil and margarine; pickled products such as "fukujin-zuke (sliced vegetables picked in soy sauce)", "bettara-zuke (fresh radish pickles)", "senmai-zuke" and "rakkyo-zuke (pickled shallots)"; premixes for pickled products such as "takuan-zuke-no-moto" and "hakusai- zuke-no-moto"; meat products such as ham and sausage; fish meat products such as fish meat ham, fish meant sausage, "kamaboko (boiled fish paste)", "chikuwa (literally bamboo wheels)" and "hanpen"; relishes such as "uni-no-shiokara (salted guts of sea urchin)", "ika-no-shiokara (salted guts of squid)", "su-konbu", "saki-surume" and "fugu-no-mirinboshi"; "tsukudani (food boiled down in soy sauce)" such as those of "nori (dried seaweed)", "sansai (mountain vegetables)", "surume (dried squid)", small fish and shellfish; daily dishes such as "nimame (cooked beans)", potato salad, "konbu-maki (tangle roll)" and "tenpura (deep-fried foods)"; egg and milk products such as "kinshi-tamago", milk beverage, butter and cheese; bottled and canned products such as those of meat, fish meat, fruit and vegetable; alcoholic drinks such as synthetic sake, "zojo-shu", liqueur, wine and whisky; beverages such as coffee, cocoa, juice, carbonated beverage, lactic acid beverage and lactobacillus beverage; premixes and instant foodstuffs such as pudding premix, hot cake premix, instant juice, instant coffee and "sokuseki-shiruko (premix of adzuki-bean soup with rice cake)". Furthermore, alpha-glycosyl rutin can be favorably incorporated as a vitamin P-enriching agent, antioxidant and taste-improving agent in feeds and pet foods for domestic animals and poultries including pet animals such as honey bee, silkworm and pet fish.

In addition to the use as a uv-absorbent and deterioration-preventing agent for plastics, alpha-glycosyl rutin can be favorably incorporated in tobaccos, cigarets, pharmaceuticals including preventive and remedy for susceptive diseases, and cosmetics including skin-refining agent and skin-whitening agent in solid, paste or liquid; for example, tobacco, cigaret, troche, cod-liver oil drop, vitamin composition, oral refreshing agent, cachou, gargle, intubation feeding, internal medicine, injection, dentifrice, lipstick, lip cream and sunscreening.

The wording "susceptive diseases" as referred to in the invention means those which are prevented and/or treated with alpha-glycosyl rutin; for example, viral diseases, bacterial diseases, traumatic diseases, immunopathies, rheumatism, diabetes, circulatory diseases and malignant tumors The shape and form of pharmaceuticals for susceptive diseases can be freely chosen to meet to their final use; for example, liquid pharmaceuticals such as nebula, collyrium, collunarium, collutory and injection, paste pharmaceuticals such as ointment, cataplasm and cream, and solid pharmaceuticals such as powder, granule, capsule and tablet.

In the preparation of such a pharmaceutical, one or more ingredients, for example, remedy, biologically-active substance, antibiotic, adjuvant, filler, stabilizer, coloring agent and flavoring agent, can be suitably used in combination, if necessary.

The dose is adequately changed dependent on the alpha-glycosyl rutin content, administration route and administration frequency; usually, about 0.001–50.0g-/day/adult as alpha-glycosyl rutin.

Cosmetics can be prepared similarly as in pharmaceuticals.

In use, alpha-glycosyl rutin is incorporated in products by conventional method, for example, mixing, kneading, dissolving, soaking, permeating, spreading, applying, spraying and injecting, before completion of their processing.

The following experiment will demonstrate the non-toxicity of the alpha-glycosyl rutin of the invention.

EXPERIMENT

An alpha-glycosyl rutin specimen, obtained by the method in Example A-3, was orally administered to 7 week-old dd mice for acute toxicity test. As the result, no mouse died when administered with up to 5g alpha-glycosyl rutin, and higher dose was difficult.

These confirmed that the specimen was extremely low in toxicity.

Another alpha-glycosyl rutin specimen, obtained by the method in Example A-2, was tested similarly as above to obtain the same result, confirming that the toxicity of this specimen was extremely low.

The following Examples A and Examples B will illustrate the preparation and uses of alpha-glycosyl rutin respectively.

EXAMPLE A-1

L. Alpha-glycosyl rutin

Three parts by weight of rutin and 15 parts by weight of dextrin (DE 18) were mixed in 97 parts by weight of 80° C water to obtain a high-rutin content liquid which was then added with 20 units/g dextrin of cyclomaltodextrin glucanotransferase derived from *Bacillus stearothermophilus*, commercialized by Hayashibara Biochemical, Inc., Okayama, Japan, and allowed to react for 64 hours under stirring conditions while keeping the liquid at pH 6.0 and 75° C.

Paper-chromatographic analysis of the reaction mixture revealed that about 85% of the rutin was converted into alpha-glycosyl rutins such as alpha-glucosyl rutin, alpha-maltosyl rutin, alpha-maltotriosyl rutin, alpha-maltotetraosyl rutin and alpha-maltopentaosyl rutin.

Thereafter, the reaction mixture was heated to inactivate the remaining enzyme and filtered, after which the filtrate was concentrated to obtain an alpha-glycosyl rutin syrup additionally containing an amylaceous substance in the yield of about 90% against the weight of the starting materials, on the dry solid basis (d.s.b.).

The product is favorably usable as a highly-safe, natural yellow coloring agent, antioxidant, stabilizer, fading-preventing agent, quality-improving agent, preventive, remedy and uv-absorbent in foods, beverages, tobaccos, cigarets, feeds, pet foods, pharmaceuticals for susceptive diseases, cosmetics and plastics, in addition to the use in an agent directed to enrich a highly water-soluble vitamin P.

EXAMPLE A-2

Alpha-glucosyl rutin

One part by weight of an alpha-glycosyl rutin syrup additionally containing an amylaceous substance, obtained by the method in Example A-1, was dissolved in 4 parts by weight of water, and the solution was adjusted to pH 5.0, added with 100 units/g syrup solid of glucoamylase (EC 3.2.1.3) commercialized by Seikagaku-Kogyo Co., Ltd., Tokyo, Japan, and allowed to react at 50° C. for 5 hours.

Paper-chromatographic analysis of the reaction mixture revealed that the alpha-glycosyl rutin was converted into alpha-glucosyl rutin.

Thereafter, the reaction mixture was heated to inactivate the remaining enzyme and filtered, after which the filtrate was applied to a column of "HP-10", a synthetic macroreticular resin commercialized by Mitsubishi Chemical Industries Ltd., Tokyo, Japan, at a flow rate of SV 2. As the result, the resin adsorbed the alpha-glycosyl rutin and remaining rutin both present in the reaction mixture, while the glucose and salts flew out through the column without causing adsorption. The column was then washed with water and applied with an aqueous ethanol having a stepwisely increasing concentration to collect fractions rich in alpha-glucosyl rutin which were then concentrated in vacuo and pulverized to obtain an alpha-glucosyl rutin powder in the yield of about 80% against the weight of the starting materials, d.s.b.

Acid hydrolysis of the alpha-glucosyl rutin yielded 1 mole of quercetin, 1 mole of L-rhamnose and 2 moles of D-glucose, while an alpha-glucosidase, obtained by extraction from pig liver and partial purification, hydrolyzed the alphaglucosyl rutin into rutin and D-glucose.

The product is favorably usable as a yellow coloring agent, antioxidant, stabilizer, fading-preventing agent, quality-improving agent, preventive, remedy and uv-absorbent in foods, beverages, tobaccos, cigarets and pharmaceuticals for susceptive diseases, in addition to the use in an agent directed to enrich a highly-purified, readily water-soluble vitamin P.

EXAMPLE A-3

Alpha-glycosyl rutin

Four parts by weight of rutin was dissolved at pH 9.5 in 90 parts by weight of water by heating, and the solution was mixed with another mixture which was separately prepared by dissolving 20 parts by weight of dextrin (DE 8) in 10 parts by weight of water by heating. The obtained high-rutin content liquid in solution was added with 30 units/g dextrin of cyclomaltodextrin glucanotransferase, and allowed to react for 40 hours under stirring conditions while keeping the liquid at pH 8.2 and 65° C.

Paper-chromatographic analysis of the reaction mixture revealed that about 90% of the rutin was converted into alpha-glycosyl rutin.

Thereafter, the reaction mixture was heated to inactivate the remaining enzyme and filtered, after which the filtrate was applied to a column of "Amberlite XAD-7", a synthetic macroreticular resin commercialized by Rohm & Haas Co., Philadelphia, USA, at a flow rate of SV 1.5.

As the result, the column adsorbed the alpha-glycosyl rutin and remaining rutin both present in the reaction mixture, while the dextrin, oligosaccharides and salts flew out through the column without causing adsorption.

The column was then washed with water and applied with 50 v/v % aqueous ethanol to elute both alpha-glycosyl rutin and intact rutin which were then concentrated in vacuo and pulverized to obtain an alpha-glycosyl rutin power in the yield of about 140% against the weight of the starting starting rutin, d.s.b.

The product is favorably usable as a yellow coloring agent, antioxidant, stabilizer, fading-preventing agent, quality-improving agent, preventive, remedy, uv-absorbent and deterioration-preventing agent in foods, beverages, tobaccos, cigarets, feeds, pet foods, pharmaceuticals for susceptive diseases, cosmetics and plastics, in addition to the use in an agent directed to enrich a highly-purified, readily water-soluble vitamin P.

EXAMPLE A-4

Alpha-glycosyl rutin

One part by weight of rutin was dissolved with 4 parts by weight of 1N sodium hydroxide solution, neutralized by the addition of 0.01N hydrochloric acid solution, added with 5 parts by weight of dextrin (DE 10), quickly added with 10 units/g dextrin of cyclomaltodextrin glucanotransferase, and allowed to react for 40 hours while keeping the mixture at pH 6.0 and 70° C.

Paper-chromatographic analysis of the reaction mixture revealed that about 80% of the rutin was converted into alpha-glycosyl rutin.

The reaction mixture was purified, concentrated and pulverized similarly as in Example A-3 to obtain an alpha-glycosyl rutin powder in the yield of about 120% against the weight of the starting rutin, d.s.b.

Similarly as the product in Example A-3, the product is feasible as a highly-safe, natural yellow coloring agent, antioxidant, stabilizer, fading-preventing agent, quality-improving agent, preventive, remedy and uv-absorbent in various uses, in addition to the use in an agent directed to enrich a highly-purified, readily water-soluble vitamin P.

EXAMPLE A-5

Alpha-glycosyl rutin

EXAMPLE A-5(1)

Preparation of alpha-glucosidase

*Mucor javanicus* IFO 4570 was inoculated and cultivated at 30° C for 44 hours under aeration-agitation conditions in 500 parts by weight of a liquid culture medium which contained water together with 4.0 w/v % maltose, 0.1 w/v % potassium phosphate monobasic, 0.1 w/v % ammonium nitrate, 0.05 w/v % magnesium sulfate, 0.05 w/v % potassium chloride, 0.2 w/v % polypeptone and 1 w/v % calcium carbonate which had been sterilized by heating and sterilely added to the water immediately before the innoculation.

After completion of the cultivation, the mycelia was collected from the culture, added with 500 parts by weight of 4M urea in 0.5M acetate buffer (pH 5.3) per 48 parts by weight of the wet mycelia, allowed to stand at 30° C. for 40 hours and centrifuged. The supernatant was dialyzed against flowing water overnight, added with ammonium sulfate to 0.9 saturation, and allowed to stand at 4° C. overnight, after which the resultant sediment was collected, suspended in 50 parts by weight of 0.01M acetate buffer (pH 5.3) and centrifuged. The supernatant was used as an alpha-glucosidase specimen.

EXAMPLE A-5(2)

Preparation of alpha-glycosyl rutin

Five parts by weight of rutin was dissolved in 40 parts by weight of 0.5N sodium hydroxide solution by heating, adjusted to pH 9.5, and mixed with another solution which had been prepared by dissolving 20 parts by weight of dextrin (DE 30) in 10 parts by weight of water by heating. The obtained high-rutin content liquid in suspension was added with 10 parts by weight of an alpha-glucosidase specimen obtained by the method in Example A-5(1), and allowed to react for 40 hours under stirring condition while keeping the liquid at pH 8.5 and 55° C.

Paper-chromatographic analysis of the reaction mixture was revealed that about 60% of the rutin was converted into alpha-glycosyl rutin.

Thereafter, the reaction mixture was purified, concentrated and pulverized similarly as in Example A-3 to obtain an alpha-glycosyl rutin powder in the yield of about 110% against the weight of the starting rutin, d.s.b.

Similarly as the product in Example A-3, the product is feasible as a highly-safe, natural yellow coloring agent, antioxidant, stabilizer, fading-preventing agent, quality-improving agent, preventive, remedy and uv-absorbent in various uses, in addition to the use in an agent directed to enrich a readily water-soluble vitamin P.

EXAMPLE A-6

Alpha-glycosyl rutin

One part by weight of rutin and 15 parts by weight of dextrin (DE 18) were dissolved in 99 parts by weight of 50 v/v aqueous methanol prewarmed to 40° C., and the solution was cooled to 25° C., added with 20 units/g dextrin of cyclomatodextrin glucanotransferase commercialized by Hayashibara Biochemical Laboratories, Inc., Okayama, Japan, adjusted to pH 6.0 and allowed to react for 72 hours. Paper-chromatographic analysis of the reaction mixture revealed that about 80% of the rutin was converted into alpha-glycosyl rutins such as alpha-glucosyl rutin, alpha-maltosyl rutin, alpha-maltotriosyl rutin, alpha-maltotetraosyl rutin and alpha-maltopentaosyl rutin. Thereafter, the reaction mixture was concentrated in vacuo to distill out the methanol, heated to inactivate the remaining enzyme and filtered, after which the filtrate was concentrated to obtain an alpha-glycosyl rutin syrup additionally containing an amylaceous substance in the yield of about 95% against the weight of the starting material, d.s.b.

The product is favorably usable as a highly-safe, natural yellow coloring agent, antioxidant, stabilizer, fading-preventing agent, quality-improving agent, preventive, remedy and uv-absorbent in foods, beverages, tobaccos, cigarets, feeds, pet foods, pharmaceuticals for susceptive diseases, cosmetics and plastics, in addition to the use in an agent directed to enrich vitamin P.

EXAMPLE A-7

Alpha-glucosyl rutin

One part by weight of an alpha-glycosyl rutin syrup additionally containing amylaceous substances, prepared by the method in Example A-6 with a slight modification, was dissolved in 4 parts by weight of water, added with 100 units/g syrup solid of glucoamylase (EC 3.2.1.3) commercialized by Toyobo Co., Ltd., Osaka, Japan, and allowed to react at 50° C. for 5 hours. Paper-chromatographic analysis of the reaction mixture revealed that the alpha-glycosyl rutin was converted into alpha-glucosyl rutin.

Thereafter, the reaction mixture was heated to inactivate the remaining enzyme and filtered, after which the filtrate was applied to a column of "HP-10", a synthetic macroreticular resin commercialized by Mitsubishi Chemical Industries Ltd., Tokyo, Japan, at a flow rate of SV 2. As the result, the resin adsorbed the alpha-glucosyl rutin and remaining rutin both present in the reaction mixture, while the dextrin, oligosaccharides, glucose and salts flew out through the column without causing adsorption. The column was then washed with water and applied with an aqueous ethanol having a stepwisely increasing concentration to collect fractions rich in alpha-glucosyl rutin which were then concentrated in vacuo and pulverized to obtain an alpha-glucosyl rutin powder in the yield of about 80% against the weight of the starting rutin, d.s.b.

Similarly as the product in Example A-2, the product is favorably usable as a yellow coloring agent, antioxidant, stabilizer, fading-preventing agent, quality-improving agent, preventive, remedy and uv-absorbent in foods, beverages, tobaccos, cigarets, pharmaceuticals for susceptive diseases and cosmetics, in addition to the use in an agent directed to enrich a highly-purified, readily water-soluble vitamin P.

EXAMPLE A-8

Alpha-glycosyl rutin

One part by weight of rutin was dissolved in 5 parts by weight of 50 v/v % aqueous ethanol by heating, and the solution was mixed with another solution which had been separately prepared by dissolving 10 parts by weight of dextrin (DE 8) in 45 parts by weight of water by heating. The mixture was added with 10 units/g dextrin of cyclomaltodextrin glucanotransferase, adjusted to pH 6.0 and allowed to react at 50° C for 24 hours.

Paper-chromatographic analysis of the reaction mixture revealed that about 90% of the rutin was converted into alpha-glycosyl rutin.

Thereafter, the reaction mixture was concentrated in vacuo to distill out the ethanol, heated to inactivate the remaining enzyme and filtered, after which the filtrate was applied to a column of "Amberlite XAD-7", a synthetic macroreticular resin commercialized by Rohm & Haas Co., Philadelphia, USA, at a flow rate of SV 1.5.

As the result, the resin adsorbed the alpha-glycosyl rutin and remaining rutin both present in the reaction mixture, while dextrin, oligosaccharides and salts flew out through the column without causing adsorption.

The column was then washed with water and applied with 50 v/v % aqueous ethanol to elute the alpha-glycosyl rutin and remaining rutin which were then concentrated and pulverized to obtain an alpha-glycosyl rutin powder in the yield of about 140% against the weight of the starting rutin, d.s.b.

The product is favorably usable as a highly-safe, natural yellow coloring agent, antioxidant, stabilizer, fading-preventing agent, quality-improving agent, preventive, remedy and uv-absorbent in foods, beverages, tobaccos, cigarets, feeds, pet foods, pharmaceuticals for susceptive diseases, cosmetics and plastics, in addition to the use in an agent directed to enrich a readily water-soluble vitamin P.

EXAMPLE A-9

Alpha-glycosyl rutin

One part by weight of rutin was dissolved in 5 parts by weight of 60 v/v % aqueous ethanol by heating, and the resultant solution was mixed with another solution which had been separately prepared by dissolving 20 parts by weight of dextrin (DE 30) in 27 parts by weight of water by heating. The mixture was added with 8 parts by weight of an alpha-glucosidase specimen obtained by the method in Example A-5(1), and allowed to react at 40° C for 40 hours while keeping the mixture at pH 5.3.

Paper-chromatographic analysis of the reaction mixture revealed that about 60% of the rutin was converted into alpha-glycosyl rutin.

Thereafter, the reaction mixture was concentrated in vacuo to distill out the ethanol, purified, concentrated and pulverized similarly as in Example A-8 to obtain an alphaglycosyl rutin powder in the yield of about 110% against the weight of the starting rutin, d.s.b.

Similarly as the product in Example A-8, the product is feasible as a highly-safe, natural yellow coloring agent, antioxidant, stabilizer, fading-preventing agent, quality-improving agent, preventive, remedy and uv-absorbent in various uses, in addition to the use in an agent directed to enrich a readily water-soluble vitamin P.

EXAMPLE A-10

Alpha-glycosyl rutin

One part by weight of an alpha-glycosyl rutin syrup additionally containing amylaceous substances, prepared by the method in Example A-6 with a slight modification, was dissolved in 4 parts by weight of water, added with 100 units/g syrup solid of beta-amylase (EC 3.2.1.2) commercialized by Toyobo Co., Ltd., Osaka, Japan, and allowed to react at 50° C for 5 hours.

Paper-chromatographic analysis of the reaction mixture revealed that the alpha-glycosyl rutin was converted into an alpha-glycosyl rutin mainly composed of alpha-glucosyl rutin and alpha-maltosyl rutin.

Thereafter, the reaction mixture was heated to inactivate the remaining enzyme and filtered, after which the filtrate was applied to a column of "HP-10", a synthetic macroreticular resin commercialized by Mitsubishi Chemical Industries, Ltd., Tokyo, Japan, at a flow rate of SV 2. As the result, the resin adsorbed the alpha-glycosyl rutin and remaining rutin both present in the reaction mixture, while the maltose, oligosaccharides, glucose and salts flew out through the column without causing adsorption. The column was then washed with water and applied with an aqueous ethanol having a stepwisely increasing concentration to obtain fractions rich in alpha-glycosyl rutin which were then concentrated in vacuo and pulverized to obtain an alpha-glycosyl rutin powder in the yield of about 85% against the weight of the starting rutin, d.s.b.

Glucoamylase hydrolyzed the alpha-glycosyl rutin into alpha-glucosyl rutin and D-glucose, while an alpha-glucosidase, prepared by the extraction from pig liver and partial purification, hydrolyzed the alpha-glycosyl rutin into rutin and D-glucose.

The product is favorably usable as a yellow coloring agent, antioxidant, stabilizer, fading-preventing agent, quality-improving agent, preventive, remedy and uv-absorbent in foods, beverages, tobaccos, cigarets, feeds, pet foods, pharmaceuticals for susceptive diseases, cosmetics and plastics, in addition to the use in an agent directed to enrich a highlypurified, readily water-soluble vitamin P.

EXAMPLE B-1

Hard candy

Fifteen hundred parts by weight of "MABIT®", a hydrogenated maltose syrup commercialized by Hayashibara Shoji, Inc., Okayama, Japan, was heated, concentrated to a moisture content below about 2%, and mixed to homogeneity with 15 parts by weight of citric acid, 1 part by weight of an alpha-glycosyl rutin powder obtained by the method in Example A-3 and a small amount of lemon flavor, after which the mixture was molded and packaged in usual manner to obtain a hard candy.

The product is a yellow colored, vitamin P-enriched, low-cariogenic and low-caloric lemon candy.

EXAMPLE B-2

"Fuki-no-mizuni (Boiled bog rhubarb)"

Fresh bog rhubargs were pared, cut into short sticks, soaked in a diluted saline, and boiled down in a liquid containing an alpha-glycosyl rutin syrup obtained by the method in Example A-1 and "Aoiro Ichi-go (Blue No.1)", a green coloring agent, to obtain a freshly green "fuki-no-mizuni)".

The product pleases the eyes when arranged in Japanese traditional cuisines, as well as exhibiting physiological activity as a dietary fiber.

EXAMPLE B-3

"Gyuhi (starch paste)"

One part by weight of waxy rice starch was mixed with 1.2 parts by weight of water, and the mixture was mixed to homogeneity with 1.5 parts by weight of sucrose, 0.7 parts by weight of "SUNMALT®", a crystalline beta-maltose commercialized by Hayashibara Co., Ltd., Okayama, Japan, 0.3 parts by weight of starch syrup and 0.2 parts by weight of an alpha-glycosyl syrup obtained by the method in Example A-6 while gelatinizing by heating, molded and packaged in usual manner to obtain "gyuhi".

The product is a Japanese-style confectionery which looks like "kibi-dango (millet dumpling)", and is excellent in flavor and biting properties.

EXAMPLE B-4

Mixed sweetener

A mixed sweetener was obtained by mixing 100 parts by weight of honey, 50 parts by weight of isomerized sugar, 2 parts by weight of "kurozato (unrefined sugar)" and 1 part by weight of an alpha-glycosyl rutin powder obtained by the method in Example A-9.

The product is a vitamin P-enriched sweetener, and suitable for health food.

EXAMPLE B-5

Cream filling

A cream filling was obtained by mixing in usual manner 1,200 parts by weight of "FINETOSE®", a crystalline alpha-maltose commercialized by Hayashibara Co., Ltd., Okayama, Japan, 1,000 parts by weight of shortening, 10 parts by weight of an alpha-glycosyl rutin powder obtained by the method in Example A-8, 1 part by weight of lecithin, 1 part by weight of lemon oil and 1 part by weight of vanilla oil to homogeneity.

The product is a yellow colored, vitamin P-enriched cream filling which is excellent in taste, flavor, melting and biting properties, and is preventive to the oxidation of the fatty ingredients.

EXAMPLE B-6

Orange juice

Fifty parts by weight of a fresh orange juice, 0.1 part of citric acid, 5 parts by weight of sucrose, 0.5 parts by weight of an alpha-glycosyl rutin powder obtained by the method in Example A-5, 0.1 part by weight of L-ascorbic acid (vitamin C), flavor and 46 parts by weight of water were mixed, and the mixture was distributed in vessels and pasteurized in usual manner to obtained the captioned product.

The product is a vitamin P- and vitamin C-enriched orange juice excellent in color, taste and flavor.

EXAMPLE B-7

Tablet

Twenty parts by weight of ascorbic acid was mixed to homogeneity with 13 parts by weight of crystalline beta-maltose, 4 parts by weight of cornstarch and 3 parts by weight of an alpha-glycosyl rutin obtained by the method in Example A-7, and the resultant was tabletted with a 20R punch, diameter of 12 mm.

The product is an easily swallowable vitamin composition containing ascorbic acid and alpha-glycosyl rutin, wherein the ascorbic acid is excellently stable.

EXAMPLE B-8

Capsule

Ten parts by weight of calcium acetate monohydrate, 50 parts by weight of magnesium L-lactate trihydrate, 57 parts by weight of maltose, 20 parts by weight of an alpha-glucosyl rutin powder obtained by the method in Example A-2, 12 parts by weight of a gamma-cyclodextrin inclusion compound containing 20% eicosapentaenoic acid were mixed to homogeneity, and the mixture was fed to a granulator and encapsulated in gelatine to obtain capsules, 150 mg each.

The product is preventive to the oxidation of the eicosapentaenoic acid, and favorably usable as a high-quality blood cholesterol lowering agent, immunopotentiator and skin-refining agent in preventive and remedy for susceptive diseases, as well as in foodstuffs directed to the maintenance and promotion of health.

EXAMPLE B-9

Ointment

One part by weight of sodium acetate trihydrate, 4 parts by weight of DL-calcium lactate and 10 parts by weight of glycerine were mixed to homogeneity, and the mixture was added to another mixture of 50 parts by weight of vaseline, 10 parts by weight of vegetable wax, 10 parts by weight of lanolin, 14.5 parts by weight of sesame oil, 1 part by weight of an alpha-glycosyl rutin powder obtained by the method in Example A-4 and 0.5 parts by weight of peppermint oil, and mixed to homogeneity to obtain an ointment.

The product is antioxidative, highly stable, and favorably usable as a high-quality sun-screening, skin-refining agent, skin-whitening agent and promoter for healing injury and burn.

EXAMPLE B-10

Injection

An alpha-glucosyl rutin powder obtained by the method in Example A-7 was dissolved in water, and sterilely filtered in usual manner to obtain a pyrogen-free solution which was then distributed to 20ml glass vials to give an alpha-glucosyl rutin content of 200mg, dried in vacuo and sealed to obtained the captioned product.

The product is intramuscularly and intravenously administrable alone or in combination with vitamins and minerals. The product requires no cold storage, and exhibits an excellently high solubility in saline when in use.

Besides supplementing vitamin P, the product functions as an antioxidant to remove activated oxygen and suppress the formation of lipoperoxides, therefore is favorably usable in preventive and remedy for various diseases including viral diseases, bacterial diseases, circulatory diseases and malignant tumors.

EXAMPLE B-11

Injection

Six parts by weight of sodium chloride, 0.3 parts by weight of potassium chloride, 0.2 parts by weight of calcium chloride, 3.1 parts by weight of sodium lactate, 45 parts by weight of maltose and 2 parts of an alpha-glucosyl rutin powder obtained by the method in Example A-2 were dissolved in 1,000 parts by weight of water, and sterilely filtered in usual manner, after which 250ml aliquots of the pyrogen-free solution were distributed to sterilized plastic vessels to obtain the captioned product.

The product supplements, in addition to vitamin P, calorie and minerals, therefore is suitable for injection directed to remove activated oxygen and to suppress the formation of lipoperoxides. Thus, the product is favorably usable in preventive and remedy for various diseases including viral diseases, bacterial diseases, circulatory diseases and malignant tumors, as well as in the restoration of health during and before suffering from diseases.

EXAMPLE B-12

Intubation nutrient

Twenty four gram aliquots of a composition consisting of 20 parts by weight of crystalline alpha-maltose, 1.1 parts by weight of glycine, 0.18 parts by weight of sodium glutamate, 1.2 parts by weight of sodium chloride, 1 part by weight of citric acid, 0.4 parts by weight of calcium lactate, 0.1 part by weight of magnesium carbonate, 0.1 part by weight of an alpha-glycosyl rutin powder obtained by the method in Example A-8, 0.01 part by weight of thyamine and 0.01 part by weight of riboflavin were packed in laminated aluminum bags, and heat-sealed to obtain the captioned product.

In use, one bag of the product is dissolved in about 300–500ml of water, and the solution is favorably usable as an intubation nutrient directed to oral and parenteral administration to the nasal cavity, stomach and intestine.

EXAMPLE B-13

Bath liquid

A bath liquid was obtained by mixing 21 parts of DL-sodium lactate, 8 parts by weight of sodium pyruvate, 5 parts by weight of an alpha-glycosyl rutin syrup obtained by the method in Example A-1 and 40 parts by weight of ethanol with 26 parts by eight of refined water and appropriate amounts of coloring agent and flavoring agent.

The product is suitable for skin-refining agent and skin-whitening agent, and is diluted by 100–10,000 folds in bath water when in use. The product is favorably usable as cleansing liquid, astringent and moisture liquid.

EXAMPLE B-14

Milky lotion

One half part by weight of polyoxyethylene behenyl ether, 1 part by weight of polyoxyethylene sorbitol tetraoleate, 1 part by weight of oil-soluble glyceryl monostearate, 0.5 parts by weight of pyruvic acid, 0.5 parts by weight of behenyl alcohol, 1 part by weight of avocado oil, 1 part by weight of an alpha-glycosyl rutin powder obtained by the method in Example A-3 and appropriate amounts of vitamin E and antiseptic were dissolved by heating in usual manner, and the solution was added with 1 part by weight of L-sodium lactate, 5 parts by weight of 1,3-butylene glycol, 0.1 part by weight of caoboxyvinyl polymer and 85.3 parts by weight of refined water, emulsified with a homogenizer, added with an appropriate amount of flavoring agent, and mixed by stirring to obtained the captioned product.

The product is antioxidative, highly stable and favorably usable as a high-quality sun-screening, skin-refining agent and skin-whitening agent.

EXAMPLE B-15

Cosmetic cream

Two parts by weight of polyoxyethylene glycol monostearate, 5 parts by weight of self-emulsifying glycerine monostearate, 2 parts by weight of an alpha-glucosyl rutin powder obtained by the method in Example A-2, 1 part by weight of liquid paraffin, 10 parts by weight of glyceryl triactanate and an appropriate amount of antiseptic were dissolved by heating in usual manner, and the mixture was added with 2 parts by weight of L-lactic acid, 5 parts by weight of 1,3-butylene glycol and 66 parts by weight of refined water, emulsified with a homogenizer, added with an appropriate amount of flavoring agent, and mixed by stirring to obtained the captioned product.

The product is antioxidative, highly stable and favorably usable as a high-quality santan cream, skin-refining agent and skin-whitening agent.

EXAMPLE B-16

Antioxidant

An antioxidant was prepared by mixing 10 parts by weight of an alpha-glycosyl rutin powder obtained by the method in Example A-10, 2 parts by weight of vitamin $E_2$, 0.1 part by weight of lecithin and 0.5 parts by weight of sodium citrate were mixed to homogeneity.

The product is favorably usable as an antioxidant, stabilizer and quality-improving agent in fatty food substances such as margarine and butter cream, pharmaceuticals for susceptive diseases such as unsaturated fatty acids, oil-soluble vitamin and oil-soluble hormones, and cosmetics such as cream lotion and cosmetic cream by incorporating thereto in an amount of about 0.01–5.0 w/w %.

EXAMPLE B-17

Antioxidant

An antioxidant was prepared by mixing to homogeneity 10 parts by weight of an alpha-glucosyl rutin powder obtained by the method in Example A-2 and 0.2 parts by weight of sodium citrate.

The product is favorably usable as an antioxidant, stabilizer and quality-improving agent in fatty food substances such as margarine and butter cream, pharmaceuticals for alphaglycosyl rutin-susceptive diseases such as unsaturated fatty acids, oil-soluble vitamin and oil-soluble hormones, and cosmetics such as cream lotion and cosmetic cream by incorporating thereinto in an amount about 0.01–5.0 w/w %. Furthermore, the product is favorably usable as antioxidant, stabilizer, fading-preventing agent and quality-improving agent in foods and beverages containing a readily-fading natural pigment by incorporating thereinto in an amount of about 0.01–2.0 w/w %.

As described above, the present invention is based on the finding that in the preparation of alpha-glycosyl rutin the initial concentration for rutin can be increased to about 5-folds or more, desirably, about 10–200-folds of that attainable by conventional method by allowing a saccharide-transferring enzyme to act on a high-rutin content liquid which contains a high-concentration rutin together with an amylaceous substance, desirably, on a high-rutin content suspension or a high-rutin content solution which is obtainable by dissolving rutin at an alkaline pH or dissolving rutin in an organic solvent. Thus, alpha-glycosyl rutin is readily formed at a high concentration.

Furthermore, we found that an alpha-glycosyl rutin comprising alpha-glucosyl rutin and/or alpha-maltosyl rutin is obtainable by first allowing a saccharide-transferring enzyme to a solution containing rutin together with an amylaceous substance, then allowing an amylase to act of the resultant mixture.

We also found that the alpha-glycosyl rutin present in a reaction mixture can be purified by allowing the mixture to contact with a synthetic macroreticular resin. Particularly in case that the reaction mixture contain an organic solvent, the alpha-glycosyl rutin can be purified similarly as above by first decreasing the concentration of the organic solvent, then allowing the reaction mixture to contact with a synthetic macroreticular resin.

These extremely reduce and save the water and energy and energy in the reaction and purification processes for alpha-glycosyl rutin, and extremely facilitate its commercialization.

The alpha-glycosyl rutin obtained in this way is characterized in that it is excellently high in water-solubility, light-resistance and stability, and is hydrolyzable by the in vivo enzyme system into rutin and glucose to exhibit the physiological properties inherent to rutin. Because of these, the alpha-glycosyl rutin is favorably usable as a yellow coloring agent, antioxidant, stabilizer, fade-preventing agent, quality-improving agent, preventive, remedy, uv-absorbent and deterioration-preventing agent in foods, beverages, tobaccos, cigarets, feeds, pet foods, pharmaceuticals for susceptive diseases, cosmetics including skin-refining agent, melanin formation-suppressing agent and skin-whitening agent, and plastics, in addition to the use in an agent directed to enrich a highly-safe, natural vitamin P.

Accordingly, the present invention is extremely significant in food, beverage, cosmetic, pharmaceutical and plastic industries in view of the establishment of industrial-scale production and practical uses for alpha-glycosyl rutin.

We claim:

1. In the method of preparing alpha-glycosyl rutin by allowing a saccharide-transferring enzyme to act on a liquid which contains rutin together with an amylaceous substance, said enzyme being capable of transferring equimolar or more glucose residues from the amylaceous substance to the rutin, under conditions sufficient to form alpha-glycosyl rutin, and then recovering the alpha-glycosyl rutin, the improvement wherein:
   said liquid containing rutin and amylaceous substance includes at least about 0.5 w/v % rutin.

2. A method in accordance with claim 1, wherein said liquid containing rutin and amylaceous substance contains said rutin in suspension.

3. A method in accordance with claim 1, wherein said liquid containing rutin and amylaceous substance is obtained by dissolving the rutin int he liquid at an alkaline pH.

4. A method in accordance with claim 1, wherein said liquid containing rutin and amylaceous substance is obtained by dissolving the rutin in an aqueous organic solvent.

5. A method in accordance with claim 1, wherein said liquid containing rutin and amylaceous substance is obtained by dissolving the rutin in an aqueous alkaline solution, mixing with an aqueous organic solvent, and neutralizing, prior to the saccharide-transfer reaction.

6. A method in accordance with claim 1, wherein said liquid containing rutin and amylaceous substance further contains about 3–70 w/v % organic solvent, and further including the steps of, prior to said recovery step:
   decreasing the concentration of the organic solvent; and
   purifying the alpha-glycosyl rutin by allowing the aqueous solution to contact a synthetic macroreticular resin.

7. A method in accordance with claim 1, wherein the alpha-glycosyl rutin being produced in alpha-glucosyl rutin and/or alpha-maltosyl rutin, further including the step of, prior to said recovery step:
   allowing glucoamylase (EC 3.2.1.3) or beta-amylase (EC 3.2.1.2) to act on the mixture resulting form said saccharide-transfer step, to form alpha-glucosyl rutin and/or alpha-maltosyl rutin.

8. A method in accordance with claim 2, further including the step of, prior to said recovery step, purifying the mixture solution resulting from said glucoamylase or beta-amylase action step by contact of said mixture solution with a synthetic macroreticular resin.

9. The process of claim 1, wherein said saccharide-transferring enzyme is a member selected from the group consisting of alpha-glucosidase (EC 3.2.1.20), cyclomaltodextrin glucanotransferase (EC 2.4.1.19), and alpha-amylase (EC 3.2.1.1.).

10. The process of claim 1, wherein said amylaceous substance is a member selected from the group consisting of maltooligosaccharide, partial starch hydrolysate, liquefied starch, and gelatinized starch.

11. The process of claim 1, wherein the concentration of rutin is about 0.5-50-folds higher than that of the amylaceous substance.

12. The process of claim 1, wherein said saccharide-transferring enzyme is allowed to act on the high-rutin content liquid at a pH in the range of 3–10 and a temperature in the range of 10°–90° C.

13. The process of claim 1, wherein said alpha-glycosyl rutin is an alpha-glucosyl rutin.

14. In the method or preparing foods and beverages containing alpha-glycosyl rutin by allowing a saccharide-transferring enzyme to act on a liquid which contains rutin together with an amylaceous substance, said enzyme being capable of transferring equimolar or more glucose residues from the amylaceous substance to the rutin, under conditions sufficient to form alpha-glycosyl rutin, recovering the alpha-glycosyl rutin, and incorporation the alpha-glycosyl rutin int he food or beverage, the improvement wherein:
   said liquid containing rutin and amylaceous substance includes at least about 0.5 w/v % rutin.

15. The process of claim 14, wherein said alpha-glycosyl rutin is incorporated in an amount at least 0.001 w/t/ %.

16. The process of claim 14, wherein said alpha-glycosyl rutin is an alpha-glucosyl rutin.

17. In the method of preparing pharmaceuticals for diseases which are prevented and/or treated with alpha-glycosyl rutin by allowing a saccharide-transferring enzyme to act on a liquid which contains rutin together with an amylaceous substance, said enzyme being capable of transferring equimolar or more glucose residues from the amylaceous substance to the rutin, under conditions sufficient to form alpha-glycosyl rutin, recovering the alpha-glycosyl rutin, and incorporating the alpha-glycosyl rutin in the pharmaceutical, the improvement wherein:
   said liquid containing rutin and amylaceous substance includes at least about 0.5 w/v % rutin.

18. The process of claim 17, wherein said alpha-glycosyl rutin is an alpha-glucosyl rutin.

19. In the method of preparing cosmetics containing alpha-glycosyl rutin by allowing a saccharide-transferring enzyme to act on a liquid which contains rutin together with an amylaceous substance, said enzyme being capable of transferring equimolar or more glucose residues from the amylaceous substance to the rutin, under conditions sufficient to form alpha-glycosyl rutin, recovering the alpha-glycosyl rutin, and incorporating the alpha-glycosyl rutin in the cosmetic, the improvement wherein:

said liquid containing rutin and amylaceous substance includes at least about 0.5 w/v % rutin.

20. The process of claim 19, wherein said alpha-glycosyl rutin is incorporated in an amount at least 0.001 w/w %.

21. The process of claim 19, wherein said alpha-glycosyl rutin is an alpha-glucosyl rutin.

22. In the method of preparing an antioxidant containing alpha-glycosyl rutin by allowing a saccharide-transferring enzyme to act on a liquid which contains rutin together with an amylaceous substance, said enzyme being capable of transferring equimolar or more glucose residues from the amylaceous substance to the rutin, under conditions sufficient to form alpha-glycosyl rutin, recovering the alpha-glycosyl rutin, and incorporating the alpha-glycosyl rutin in the antioxidant, the improvement wherein:

said liquid containing rutin and amylaceous substance includes at least about 0.5 w/v % rutin.

23. The process of claim 22, wherein said alpha-glycosyl rutin is an alpha-glucosyl rutin.

* * * * *